(12) United States Patent
Shaw et al.

(10) Patent No.: US 7,727,535 B2
(45) Date of Patent: Jun. 1, 2010

(54) PLATELET GLYCOPROTEIN IB ALPHA VARIANT FUSION POLYPEPTIDES AND METHODS OF USE THEREOF

(75) Inventors: Gray Shaw, Milton, MA (US); Dianne Sako, Medford, MA (US); Ravindra Kumar, Acton, MA (US); Jin Xu, Dracut, MA (US)

(73) Assignee: Wyeth, Madison, NJ (US)

( * ) Notice: Subject to any disclaimer, the term of this patent is extended or adjusted under 35 U.S.C. 154(b) by 50 days.

(21) Appl. No.: 10/868,371

(22) Filed: Jun. 14, 2004

(65) Prior Publication Data

US 2005/0089888 A1   Apr. 28, 2005

Related U.S. Application Data

(60) Provisional application No. 60/477,525, filed on Jun. 11, 2003.

(51) Int. Cl.
*A61K 39/00* (2006.01)
*C07K 17/00* (2006.01)

(52) U.S. Cl. .............. 424/185.1; 424/192.1; 424/193.1; 530/391.1; 530/395; 530/326; 514/12

(58) Field of Classification Search ............ 514/2; 435/69.1, 69.6; 424/178.1, 94.63
See application file for complete search history.

(56) References Cited

U.S. PATENT DOCUMENTS

| | | | |
|---|---|---|---|
| 5,225,538 A | 7/1993 | Capon et al. | 530/387.3 |
| 5,340,727 A | 8/1994 | Ruggeri et al. | 435/69.6 |
| 5,428,130 A | 6/1995 | Capon et al. | 530/350 |
| 5,455,165 A | 10/1995 | Capon et al. | 435/64.7 |
| 5,514,582 A | 5/1996 | Capon et al. | 435/252.3 |
| 5,516,964 A | 5/1996 | Umansky et al. | 585/751 |
| 5,593,959 A | 1/1997 | Miller et al. | 514/8 |
| 5,714,147 A | 2/1998 | Capon et al. | 424/178.1 |
| 6,136,310 A | 10/2000 | Hanna et al. | 424/154.1 |
| 6,177,059 B1 | 1/2001 | Matsuda et al. | 424/1.21 |
| 6,277,975 B1 | 8/2001 | Larsen et al. | 536/23.4 |
| 2003/0091576 A1* | 5/2003 | Shaw et al. | 424/178.1 |

FOREIGN PATENT DOCUMENTS

| | | |
|---|---|---|
| EP | 0 317 278 A2 | 5/1989 |
| EP | 1 074 564 | 2/2001 |
| WO | WO 98/08949 | 3/1998 |
| WO | WO 99/51642 | 10/1999 |
| WO | WO 02/063003 A2 | 8/2002 |

OTHER PUBLICATIONS

Sergei, T.A., et al. 2000 J of Virology 74(11): 5101-5107.*
Yuan, S-M., et al. 1998 Proteins: Structure, Function, and Genetics 30: 136-143.*
Seffernick, J.L., et al. Melamine Deaminase and Atrazine Chlorohydrolase: 98 Percent Identical but Functionally Different 2001 Journal of Bacteriology 183(8): 2405-2410.*
Attwood *Science*, 290(5491):471-473 (2000).
Cole, et al. *J. Immunol.*, 159(7):3613-3621 (1997).
Database Biosis Online Accession No. PREV200200250180, abstract (Nov. 16, 2001).
Database Biosis Online Accession No. PREV200200220561, abstract (Nov. 16, 2001).
Database Biosis Online Accession No. PREV200300080165, abstract (Nov. 5, 2002).
Database Biosis Online Accession No. prev200400161655, abstract (Nov. 16, 2003).
Dong, et al. *J. Biol. Chem.* 275(36): 27663-27670 (2000).
GenBank Accession No. BAB12083 (Aug. 26, 2000).
GenBank Accession No. AB038516 (Aug. 25, 2000).
GenBank Accession No. BAA12911 (Apr. 14, 2000).
GenBank Accession No. AAC53320 (Aug. 17, 1997).
GenBank Accession No. U91967 (Aug. 17, 1997).
Geneseq Online Database Accession No. AAY49933. (Feb. 1, 2000).
Huizinga et al. *Science*, 297:1176-1179 (2002).
Kenny et al. *Blood*, 92(1):175-183 (1998).
Lopez, et al. *Proc. Natl. Acad. Sci. USA*, 84: 5615-5619 (1987).
Marchese et al. *J. Biol. Chem.*, 270(16):9571-9578 (1995).
Metzler et al. *Nat. Struct. Biol.*, 4(7):527-531 (1997).
Miura et al. *J. Biol. Chem.*, 275(11):7539-7546 (2000).
Ngo et al. *Computational complexity, protein structure prediction, and the Levinthal paradox*, Chapter 14, pp. 433-506, Birkhauser Boston (1994).
Scalia, et al. *Circ. Res.*, 84(1):93-102 (1999).
Skolnick et al. *TIBTECH*, 18(1):34-39 (2000).
Titanl, et al. *Proc. Natl. Acad. Sci. USA*, 84: 5610-5614(1987).
International Search Report for PCT/US2004/019057, mailed on Mar. 4, 2005.
Shaw et al., "A recombinant soluble Ig fusion orm of human GPIbα inhibits platelet aggregation and recurrent coronary cyclic flow reduction in a canine model", Abstract only, in the 43rd Annual Meeting of the American Society of Hematology, part 1, and *Blood*, 98(11):704a (2001).

* cited by examiner

*Primary Examiner*—Maryam Monshipouri
*Assistant Examiner*—Marsha M Tsay
(74) *Attorney, Agent, or Firm*—Mintz, Levin, Cohen, Ferris, Glovsky & Popeo P.C.; Ivor R. Elrifi; David E. Johnson

(57) ABSTRACT

The present invention provides compositions and methods for treating or preventing vascular-associated disorders.

3 Claims, 3 Drawing Sheets

SEQUENCE LISTING

```
<160> NUMBER OF SEQ ID NOS: 10

<210> SEQ ID NO 1
<211> LENGTH: 290
<212> TYPE: PRT
<213> ORGANISM: Homo sapiens

<400> SEQUENCE: 1

His Pro Ile Cys Glu Val Ser Lys Val Ala Ser His Leu Glu Val Asn
  1               5                  10                  15

Cys Asp Lys Arg Asn Leu Thr Ala Leu Pro Pro Asp Leu Pro Lys Asp
             20                  25                  30

Thr Thr Ile Leu His Leu Ser Glu Asn Leu Leu Tyr Thr Phe Ser Leu
         35                  40                  45

Ala Thr Leu Met Pro Tyr Thr Arg Leu Thr Gln Leu Asn Leu Asp Arg
     50                  55                  60

Cys Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190
```

```
Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Pro Glu Glu Asp Thr Glu Gly Asp Lys
        275                 280                 285

Val Arg
    290

<210> SEQ ID NO 2
<211> LENGTH: 290
<212> TYPE: PRT
<213> ORGANISM: Homo sapiens

<400> SEQUENCE: 2

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Val Asp Val Lys Ala Val Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270
```

Thr Asp Leu Tyr Asp Tyr Tyr Pro Glu Glu Asp Thr Glu Gly Asp Lys
        275                 280                 285

Val Arg
    290

<210> SEQ ID NO 3
<211> LENGTH: 302
<212> TYPE: PRT
<213> ORGANISM: Homo sapiens

<400> SEQUENCE: 3

His Pro Ile Cys Glu Val Ser Lys Val Ala Ser His Leu Glu Val Asn
  1               5                  10                  15

Cys Asp Lys Arg Asn Leu Thr Ala Leu Pro Pro Asp Leu Pro Lys Asp
             20                  25                  30

Thr Thr Ile Leu His Leu Ser Glu Asn Leu Leu Tyr Thr Phe Ser Leu
         35                  40                  45

Ala Thr Leu Met Pro Tyr Thr Arg Leu Thr Gln Leu Asn Leu Asp Arg
     50                  55                  60

Cys Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Ala Thr Arg Thr Val Val Lys Phe Pro Thr Lys Ala
    290                 295                 300

<210> SEQ ID NO 4
<211> LENGTH: 302
<212> TYPE: PRT
<213> ORGANISM: Homo sapiens

<400> SEQUENCE: 4

```
His Pro Ile Cys Glu Val Ser Lys Val Ala Ser His Leu Glu Val Asn
  1               5                  10                  15

Cys Asp Lys Arg Asn Leu Thr Ala Leu Pro Pro Asp Leu Pro Lys Asp
             20                  25                  30

Thr Thr Ile Leu His Leu Ser Glu Asn Leu Leu Tyr Thr Phe Ser Leu
              35                  40                  45

Ala Thr Leu Met Pro Tyr Thr Arg Leu Thr Gln Leu Asn Leu Asp Arg
     50                  55                  60

Cys Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
             100                 105                 110

Thr Ser Leu Pro Leu Gly Ala Leu Arg Gly Leu Gly Glu Leu Gln Glu
             115                 120                 125

Leu Tyr Leu Lys Gly Asn Glu Leu Lys Thr Leu Pro Pro Gly Leu Leu
     130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                 165                 170                 175

Leu Leu Leu Gln Glu Asn Ser Leu Tyr Thr Ile Pro Lys Gly Phe Phe
             180                 185                 190

Gly Ser His Leu Leu Pro Phe Ala Phe Leu His Gly Asn Pro Trp Leu
     195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                 245                 250                 255

Tyr Lys Tyr Pro Gly Lys Gly Cys Pro Thr Leu Gly Asp Glu Gly Asp
             260                 265                 270

Thr Asp Leu Tyr Asp Tyr Pro Glu Glu Asp Thr Glu Gly Asp Lys
             275                 280                 285

Val Ala Ala Thr Ala Thr Val Val Lys Phe Pro Thr Lys Ala
     290                 295                 300

<210> SEQ ID NO 5
<211> LENGTH: 301
<212> TYPE: PRT
<213> ORGANISM: Homo sapiens

<400> SEQUENCE: 5

His Pro Ile Cys Glu Val Ser Lys Val Ala Ser His Leu Glu Val Asn
  1               5                  10                  15

Cys Asp Lys Arg Asn Leu Thr Ala Leu Pro Pro Asp Leu Pro Lys Asp
             20                  25                  30

Thr Thr Ile Leu His Leu Ser Glu Asn Leu Leu Tyr Thr Phe Ser Leu
              35                  40                  45

Ala Thr Leu Met Pro Tyr Thr Arg Leu Thr Gln Leu Asn Leu Asp Arg
     50                  55                  60

Cys Glu Leu Thr Lys Leu Gln Val Asp Gly Thr Leu Pro Val Leu Gly
```

```
                65                  70                  75                  80
Thr Leu Asp Leu Ser His Asn Gln Leu Gln Ser Leu Pro Leu Leu Gly
                    85                  90                  95

Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
            115                 120                 125

Leu Tyr Leu Lys Gly Asn Glu Leu Lys Thr Leu Pro Pro Gly Leu Leu
        130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Val Val Asp Val Lys Ala Val Thr
225                 230                 235                 240

Ser Asn Val Ala Ser Val Gln Cys Asp Asn Ser Asp Lys Phe Pro Val
                245                 250                 255

Lys Tyr Pro Gly Lys Gly Cys Pro Thr Leu Gly Asp Glu Gly Asp Thr
            260                 265                 270

Asp Leu Tyr Asp Tyr Tyr Pro Glu Glu Asp Thr Glu Gly Asp Lys Val
        275                 280                 285

Ala Ala Thr Ala Thr Val Val Lys Phe Pro Thr Lys Ala
    290                 295                 300

<210> SEQ ID NO 6
<211> LENGTH: 290
<212> TYPE: PRT
<213> ORGANISM: Homo sapiens

<400> SEQUENCE: 6

His Pro Ile Cys Glu Val Ser Lys Val Ala Ser His Leu Glu Val Asn
  1               5                  10                  15

Cys Asp Lys Arg Asn Leu Thr Ala Leu Pro Pro Asp Leu Pro Lys Asp
                20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
        50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                    85                  90                  95

Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
            115                 120                 125

Leu Tyr Leu Lys Gly Asn Glu Leu Lys Thr Leu Pro Pro Gly Leu Leu
        130                 135                 140
```

```
Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
            165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
            195                 200                 205

Cys Asn Cys Glu Ile Leu Tyr Phe Arg Arg Trp Leu Gln Asp Asn Ala
            210                 215                 220

Glu Asn Val Tyr Val Trp Lys Gln Gly Val Asp Val Ala Ala Met Thr
225                 230                 235                 240

Ser Asn Val Ala Ser Val Gln Cys Asp Asn Ser Asp Lys Phe Pro Val
            245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
            275                 280                 285

Val Arg
    290

<210> SEQ ID NO 7
<211> LENGTH: 307
<212> TYPE: PRT
<213> ORGANISM: Homo sapiens

<400> SEQUENCE: 7

Gln Ala Thr Glu Tyr Glu Tyr Leu Asp Tyr Asp Phe Leu Pro Glu Thr
1               5                   10                  15

Glu Pro Pro Ile Cys Glu Val Ser Lys Val Ala Ser His Leu Glu Val
            20                  25                  30

Asn Cys Asp Lys Arg Asn Leu Thr Ala Leu Pro Pro Asp Leu Pro Lys
            35                  40                  45

Asp Thr Thr Ile Leu His Leu Ser Glu Asn Leu Leu Tyr Thr Phe Ser
        50                  55                  60

Leu Ala Thr Leu Met Pro Tyr Thr Arg Leu Thr Gln Leu Asn Leu Asp
65                  70                  75                  80

Arg Cys Glu Leu Thr Lys Leu Gln Val Asp Gly Thr Leu Pro Val Leu
                85                  90                  95

Gly Thr Leu Asp Leu Ser His Asn Gln Leu Gln Ser Leu Pro Leu Leu
            100                 105                 110

Gly Gln Thr Leu Pro Ala Leu Thr Val Leu Asp Val Ser Phe Asn Arg
        115                 120                 125

Leu Thr Ser Leu Pro Leu Gly Ala Leu Arg Gly Leu Gly Glu Leu Gln
130                 135                 140

Glu Leu Tyr Leu Lys Gly Asn Glu Leu Lys Thr Leu Pro Pro Gly Leu
145                 150                 155                 160

Leu Thr Pro Thr Pro Lys Leu Glu Lys Leu Ser Leu Ala Asn Asn Asn
            165                 170                 175

Leu Thr Glu Leu Pro Ala Gly Leu Leu Asn Gly Leu Glu Asn Leu Asp
            180                 185                 190

Thr Leu Leu Leu Gln Glu Asn Ser Leu Tyr Thr Ile Pro Lys Gly Phe
        195                 200                 205

Phe Gly Ser His Leu Leu Pro Phe Ala Phe Leu His Gly Asn Pro Trp
210                 215                 220
```

```
Leu Cys Asn Cys Glu Ile Leu Tyr Phe Arg Arg Trp Leu Gln Asp Asn
225                 230                 235                 240

Ala Glu Asn Val Tyr Val Trp Lys Gln Val Val Asp Val Lys Ala Val
                245                 250                 255

Thr Ser Asn Val Ala Ser Val Gln Cys Asp Asn Ser Asp Lys Phe Pro
                260                 265                 270

Val Tyr Lys Tyr Pro Gly Lys Gly Cys Pro Thr Leu Gly Asp Glu Gly
            275                 280                 285

Asp Thr Asp Leu Tyr Asp Tyr Tyr Pro Glu Glu Asp Thr Glu Gly Asp
        290                 295                 300

Lys Val Arg
305

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence:heterologous
      signal sequence

<400> SEQUENCE: 8

Met Pro Leu Leu Leu Leu Leu Leu Leu Pro Ser Pro Leu His Pro
1               5                   10                  15

<210> SEQ ID NO 9
<211> LENGTH: 41
<212> TYPE: PRT
<213> ORGANISM: Artificial Sequence
<220> FEATURE:
<223> OTHER INFORMATION: Description of Artificial Sequence:heterologous
      signal sequence

<400> SEQUENCE: 9

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
                20                  25                  30

Gly Pro Leu Leu Ala Arg Asp Arg Arg
            35                  40

<210> SEQ ID NO 10
<211> LENGTH: 224
<212> TYPE: PRT
<213> ORGANISM: Homo sapiens

<400> SEQUENCE: 10

His Thr Cys Pro Pro Cys Pro Ala Pro Glu Ala Leu Gly Ala Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
        50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95
```

-continued

```
Lys Cys Lys Val Ser Asn Lys Ala Leu Pro Val Pro Ile Glu Lys Thr
            100                 105             110

Ile Ser Lys Ala Lys Gly Gln Pro Arg Glu Pro Gln Val Tyr Thr Leu
        115             120             125

Pro Pro Ser Arg Glu Glu Met Thr Lys Asn Gln Val Ser Leu Thr Cys
        130             135             140

Leu Val Lys Gly Phe Tyr Pro Ser Asp Ile Ala Val Glu Trp Glu Ser
145             150             155                         160

Asn Gly Gln Pro Glu Asn Asn Tyr Lys Thr Thr Pro Pro Val Leu Asp
                165             170                 175

Ser Asp Gly Ser Phe Phe Leu Tyr Ser Lys Leu Thr Val Asp Lys Ser
            180             185                 190

Arg Trp Gln Gln Gly Asn Val Phe Ser Cys Ser Val Met His Glu Ala
        195             200             205

Leu His Asn His Tyr Thr Gln Lys Ser Leu Ser Leu Ser Pro Gly Lys
        210             215             220
```

PLATELET GLYCOPROTEIN IB ALPHA VARIANT FUSION POLYPEPTIDES AND METHODS OF USE THEREOF

RELATED APPLICATIONS

This application claims priority to U.S. Ser. No. 60/477,525, filed Jun. 11, 2003. The contents of this application are incorporated herein by reference in their entirety.

FIELD OF THE INVENTION

The invention relates generally to compositions and methods for treating or preventing vascular-associated disorders and more particularly to compositions including platelet glycoprotein Ibα-derived polypeptides and methods of using same.

BACKGROUND OF THE INVENTION

The deleterious effects of vascular-associated disorders such as stroke, heart attack, and artherosclerosis are thought to be caused, at least in part, by the inappropriate triggering of a vascular inflammation and repair response. The vascular inflammation and repair response involves adhesive interactions between various cell types normally found freely circulating in blood. Examples of such interactions include those that can occur between platelets, leukocytes and the inner wall of blood vessels (i.e., the vascular endothelium). Under conditions of high fluid shear forces, platelets adhere to the endothelium via an interaction between the glycoprotein (GP) Ib-IX-V complex on their surface and von Willebrand factor (vWF) present on exposed vessel subendothelium. In addition, platelets adhering to the vascular endothelium can bind and capture freely circulating platelets via vWF-mediated tethering, enabling thrombus growth through successive layers of platelets. The GPIbα chain of the GPIb-IX-V complex can also facilitate the binding of α-thrombin to the platelet surface, enhancing the thrombin-mediated cleavage of GPV and protease-activated receptors (PARs).

In contrast, leukocytes can adhere to activated endothelium either directly, or indirectly by first adhering to vWF-immobilized platelets. In both instances, leukocyte cell surface molecules that bind to either the selectin or integrin classes of adhesion receptors mediate these adhesion events. Leukocyte-platelet adhesion is thought to occur, in part, via interaction of the leukocyte surface integrin molecule MacI and the GP1b component of the platelet surface GPIb-IX-V complex.

In response to vascular disturbances such as atherosclerotic plaque rupture or mechanical injury, e.g., such as that caused by angioplasty, stent placement, cardiopulmonary bypass procedures, ischemic damage or stenosis, leukocytes and platelets can accumulate at a vascular lesion site and provide multiple adhesive substrates for one another. This accumulation of leukocytes and platelets leads to the local production of factors including, e.g., mitogens, cytokines and chemokines, causing the further undesirable progression of a vascular disease.

Therapeutic polypeptides including a vWF-binding region derived from GPIbα have been described. One such polypeptide is based on a sequence containing two amino acid substitutions (G233V M239V) in the amino acid sequence of wild-type human GPIbα. An Ig fusion protein containing 290 amino acids of the extracellular, vWF-binding domain of this variant (named GPIb2V-Ig) of this variant inhibits coronary artery thrombosis.

SUMMARY OF THE INVENTION

The invention provides improved glycoprotein-Ibα variant polypeptides that are useful as therapeutic agents for treating vascular disorders. In various embodiments, the variants show decreased aggregation, enhanced stability, decreased binding to thrombin, or two or more of these properties. One use for the glycoprotein-Ibα-protein variant polypeptides is as a fusion protein to treat vascular conditions associated with vascular inflammation, thrombosis, atherosclerosis, and angioplasty-related restenosis.

In one aspect, the polypeptide binds with lower affinity to alpha thrombin relative to binding to alpha thrombin of a polypeptide that includes the naturally occurring amino acid sequence of human GPIbα(SEQ ID NO:1) or a polypeptide, termed GPIb2V (SEQ ID NO:2), which includes the amino acid substitutions G233V and M239V relative to the amino acid sequence of SEQ ID NO:1. When the polypeptide binds with low affinity to thrombin, more thrombin is made available for thrombus formation, and undesirable bleeding in a subject is minimized. Examples of polypeptides that show reduced thrombin binding are polypeptides that include one, two, or three of the amino acid substitutions Y276F, Y278F, Y279V, or a conservative variant thereof, relative to the amino acid sequence of SEQ ID NO:1 or SEQ ID NO:2.

In some embodiments, aggregation of the polypeptide is lowered relative to aggregation of a polypeptide that includes the amino acid sequence of human SEQ ID NO:1 or SEQ ID NO:2. In some embodiments, decreased aggregation is observed during synthesis of the polypeptide in a cell. An example of a polypeptide that shows decreased aggregation is a polypeptide that includes the amino acid substitution C65S, or a conservative variant thereof, relative to the amino acid sequence of SEQ ID NO:1 or SEQ ID NO:2.

In some embodiments, the polypeptide is more resistant to proteolysis than a polypeptide that includes the amino acid sequence of SEQ ID NO:1 or SEQ ID NO:2. An example of such a polypeptide is a polypeptide includes the amino acid substitution K237V, or a conservative variant thereof, relative to the amino acid sequence of SEQ ID NO:1 or SEQ ID NO:2.

Examples of suitable polypeptides are those that have the following amino acid sequence substitutions relative to the amino acid sequence of SEQ ID NO:1 or SEQ ID NO:2: Y276F, Y276F K237V, Y276F C65S, Y276F Y278F Y279F, Y276F Y278F Y279F K237V and Y276F Y278F Y279F K237V C65S.

The polypeptides of the invention can be provided as fusion proteins. For example, the glycoprotein Ibα fusion protein can include a first polypeptide, comprising at least a region of a glycoprotein Ibα polypeptide variant, linked to a second polypeptide. In some embodiments, the second polypeptide forms a multimer, e.g., a dimer. In some embodiments, the second polypeptide includes at least a region of an immunoglobulin polypeptide.

Also provided by the invention is a nucleic acid encoding the glycoprotein-Ibα variant polypeptide, as well as vectors, cells and methods of expressing the glycoprotein-Ibα variant polypeptide using glycoprotein-Ibα variant polypeptide-encoding nucleic acids. The invention additionally includes a nucleic acid encoding a glycoprotein Ibα variant fusion polypeptide, as well as a vector containing glycoprotein Ibα fusion polypeptide-encoding nucleic acids described herein, and a cell containing the vectors or nucleic acids described herein.

Also provided by the invention is a method of inhibiting leukocyte adhesion to a biological tissue by contacting a leukocyte with a glycoprotein Ibα fusion polypeptide. The leukocyte is contacted in an amount sufficient to inhibit adherence of the leukocyte and the biological tissue.

In another aspect, the invention provides a method of treating a disorder associated with platelet activation. The method includes administering to a subject an effective amount of a glycoprotein Ibα fusion polypeptide.

Also included in the invention are pharmaceutical compositions that include glycoprotein Ibα variant polypeptides, or glycoprotein Ibα variant fusion polypeptides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
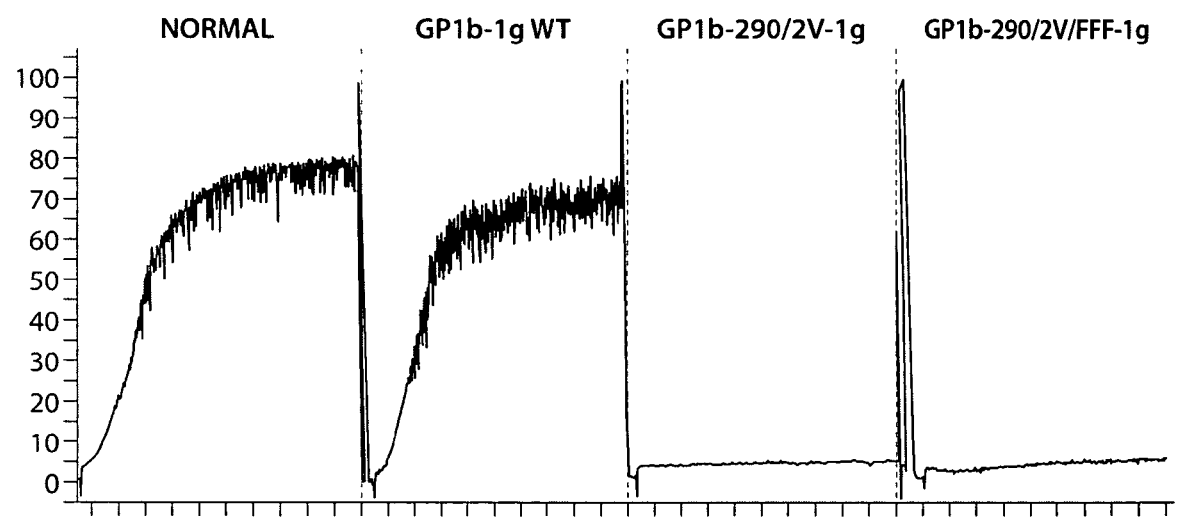
FIG. 1 is a graph showing inhibition of GPIba chimeras on ristocetin-induced human platelet aggregation. Shown are wild-type GPIba ("Normal") and GPIb-Ig WT, GPIba-290/2V-Ig, GPIba-290/2V/FFF-Ig chimeras.

Glycoprotein Ibα-derived polypeptides with decreased binding to alpha thrombin, decreased aggregation and/or increased resistance to proteolysis according to the invention are useful as therapeutic agents in, e.g., treating various conditions that benefit by inhibiting binding of activated platelet cells to vWF on vascular cells. In some embodiments, the polypeptides are provided as fusion proteins.

The protein variants of the invention with decreased thrombin binding advantageously result in decreased bleeding. Binding of thrombin to the platelet GPIbα receptor is necessary for clotting. Thrombin binding to a therapeutic soluble GPIb can augment bleeding in vivo by sequestering thrombin away from the platelet GPIbα receptor, thus reducing thrombin-induced platelet aggregation. Thus, the protein variants that show lower affinity for thrombin make the thrombin available to interact with the platelet IBα receptor, which in turn promotes clotting.

A suitable polypeptide includes an amino acid sequence with one to 15 amino acid substitutions, deletions or insertions relative to amino acids in the region between, and including, amino acids 65-279 of a naturally occurring human GPIbα protein sequence shown in SEQ ID NO:1, below, or of the variant GPIb2V, whose amino acid sequence is shown in SEQ ID NO:2, below. In one or more embodiments, the polypeptide has one or more of the following activities: (i) lower affinity binding to alpha thrombin relative to binding to alpha thrombin of a polypeptide that includes the amino acid sequence of human SEQ ID NO:1 or SEQ ID NO:2; (ii) lower aggregation relative to aggregation of a polypeptide that includes the amino acid sequence of SEQ ID NO:1 or SEQ ID NO:2; or (iii) increased resistance to proteolysis relative to a polypeptide that includes the amino acid sequence of SEQ ID NO:1 or SEQ ID NO:2.

While not wishing to be bound by theory, it is believed that these properties are based on the results of substitutions at targeted regions in the polypeptide sequence of the GPIB2V variant (SEQ ID NO:2). The change from cysteine to serine residue at position 65 (i.e., C65S) leads to inhibition of aggregation of the GPIbα molecule, in particular during a recombinant production process. The tyrosine residues found at positions 276, 278, and 279 in the wild-type sequence are normally posttranslationally modified to sulfotyrosine, which creates an anionic electrostatic interaction with alpha thrombin. Selective elimination of these tyrosine residues by converting them to phenylalanine (i.e., Y276F, Y278F, and Y279F substitutions) reduces binding to alpha thrombin (Marchese et al., J. Biol. Chem. 270:9571-78), while retaining the desired binding to vWF. A lysine to valine substitution at position 237 will prevent proteolysis at this site during the recombinant production process.

A 290 amino acid sequence fragment of a naturally occurring human glycoprotein Ibα chain is set forth below:

HPICEVSKVASHLEVNCDKRNLTALPPDLPKDTTI　(SEQ ID NO: 1)

LHLSENLLYTFSLATLMPYTRLTQLNLDRCELTKL

QVDGTLPVLGTLDLSHNQLQSLPLLGQTLPALTVL

DVSFNRLTSLPLGALRGLGELQELYLKGNELKTLP

PGLLTPTPKLEKLSLANNNLTELPAGLLNGLENLD

TLLLQENSLYTIPKGFFGSHLLPFAFLHGNPWLCN

CEILYFRRWLQDNAENVYVWKQGVDVKAMTSNVAS

VQCDNSDKFPVYKYPGKGCPTLGDEGDTDLYDYYP

EEDTEGDKVR

The amino acid sequence of the GPIb2V variant is provided below as SEQ ID NO:2. This variant is also discussed in U.S. patent application publication No. 20030091576, and its counterpart WO 02/063003.

HPICEVSKVASHLEVNCDKRNLTALPPDLPKDTTI　(SEQ ID NO: 2)

LHLSENLLYTFSLATLMPYTRLTQLNLDRCELTKL

QVDGTLPVLGTLDLSHNQLQSLPLLGQTLPALTVL

DVSFNRLTSLPLGALRGLGELQELYLKGNELKTLP

PGLLTPTPKLEKLSLANNNLTELPAGLLNGLENLD

TLLLQENSLYTIPKGFFGSHLLPFAFLHGNPWLCN

CEILYFRRWLQDNAENVYVWKQVVDVKAVTSNVAS

VQCDNSDKFPVYKYPGKGCPTLGDEGDTDLYDYYP

EEDTEGDKVR

In some embodiments, the polypeptide has no more than 12 substitutions, insertions, or deletions relative to the amino acid sequence of SEQ ID NO:1 or SEQ ID NO:2. For example, it may have 10, 8, 7, 6, 5 or fewer substitutions, insertions, or deletions relative to the amino acid sequence of SEQ ID NO:1 or SEQ ID NO:2. In some embodiments, the substitutions, insertions, or deletions are in the region between amino acids 65 and 279, inclusive.

In some embodiments, the polypeptide binds with lower affinity to alpha thrombin relative to binding to alpha thrombin of a polypeptide that includes the amino acid sequence of SEQ ID NO:1 or SEQ ID NO:2. Examples of polypeptides that show reduced binding are polypeptides that include one, two, or three of the amino acid substitutions Y276F, Y278F, Y279V, or a conservative variant thereof, relative to the amino acid sequence of SEQ ID NO:1 or SEQ ID NO:2.

In some embodiments aggregation of the polypeptide is lowered relative to aggregation of a polypeptide that includes the amino acid sequence of SEQ ID NO:1 or SEQ ID NO:2. In some embodiments, decreased aggregation is observed during synthesis of the polypeptide in a cell. An example of a polypeptide that shows decreased aggregation is a polypeptide that includes the amino acid substitution C65S, or a conservative variant thereof, relative to the amino acid sequence of SEQ ID NO:1 or SEQ ID NO:2.

In some embodiments, the polypeptide is more resistant to proteolysis than a polypeptide that includes the amino acid sequence of SEQ ID NO:1 or SEQ ID NO:2. An example of such a polypeptide is a polypeptide includes the amino acid substitution K237V, or a conservative variant thereof, relative to the amino acid sequence of SEQ ID NO:1 or SEQ ID NO:2.

In some embodiments, the polypeptide includes an amino acid sequence with one to 10 amino acid substitutions, insertions, or deletions relative to amino acids 1-290 of SEQ ID NO:1 or SEQ ID NO:2, provided that at least one of the amino acid substitutions is C65S, K237V, Y276F Y278F, Y279F, K237V.

Examples of suitable polypeptides are those that have the following amino acid sequence substitutions relative to the amino acid sequence of SEQ ID NO:1 or SEQ ID NO:2: Y276F, Y276F K237V, Y276F C65S, Y276F Y278F Y279F, Y276F Y278F Y279F K237V and Y276F Y278F Y279F K237V C65S.

The invention also includes polypeptides with one or more, e.g., 2, 3, 5, 6, 8, 10, 15 or more amino acid substitutions in polypeptides derived from glycoprotein IBα sequences in addition to those corresponding to SEQ ID NO:1 and SEQ ID NO:2. These include, e.g., GPIb302 (SEQ ID NO:3), GPIb302/2A (SEQ ID NO:4) GPIb/4X (SEQ ID NO:5), and GBIb290/1A (SEQ ID NO:6).

```
HPICEVSKVASHLEVNCDKRNLTALPPDLPKDTTI  (SEQ ID NO: 3)
LHLSENLLYTFSLATLMPYTRLTQLNLDRCELTKL
QVDGTLPVLGTLDLSHNQLQSLPLLGQTLPALTVL
DVSFNRLTSLPLGALRGLGELQELYLKGNELKTLP
PGLLTPTPKLEKLSLANNNLTELPAGLLNGLENLD
TLLLQENSLYTIPKGFFGSHLLPFAFLHGNPWLCN
CEILYFRRWLQDNAENVYVWKQGVDVKAMTSNVAS
VQCDNSDKFPVYKYPGKGCPTLGDEGDTDLYDYYP
EEDTEGDKVRATRTVVKFPTKA

HPICEVSKVASHLEVNCDKRNLTALPPDLPKDTTI  (SEQ ID NO: 4)
LHLSENLLYTFSLATLMPYTRLTQLNLDRCELTKL
QVDGTLPVLGTLDLSHNQLQSLPLLGQTLPALTVL
```

-continued
```
DVSFNRLTSLPLGALRGLGELQELYLKGNELKTLP
PGLLTPTPKLEKLSLANNNLTELPAGLLNGLENLD
TLLLQENSLYTIPKGFFGSHLLPFAFLHGNPWLCN
CEILYFRRWLQDNAENVYVWKQGVDVKAMTSNVAS
VQCDNSDKFPVYKYPGKGCPTLGDEGDTDLYDYYP
EEDTEGDKVAATATVVKFPTKA HPICEVSKVASHLEVNCDKRNLTALPPDLPKDTTI  (SEQ ID NO: 5)
LHLSENLLYTFSLATLMPYTRLTQLNLDRCELTKL
QVDGTLPVLGTLDLSHNQLQSLPLLGQTLPALTVL
DVSFNRLTSLPLGALRGLGELQELYLKGNELKTLP
PGLLTPTPKLEKLSLANNNLTELPAGLLNGLENLD
TLLLQENSLYTIPKGFFGSHLLPFAFLHGNPWLCN
CEILYFRRWLQDNAENVYVWKQVVDVKAVTSNVAS
VQCDNSDKFPVYKYPGKGCPTLGDEGDTDLYDYYPE
EDTEGDKVAATATVVKFPTKA HPICEVSKVASHLEVNCDKRNLTALPPDLPKDTTI  (SEQ ID NO: 6)
LHLSENLLYTFSLATLMPYTRLTQLNLDRCELTKL
QVDGTLPVLGTLDLSHNQLQSLPLLGQTLPALTVL
DVSFNRLTSLPLGALRGLGELQELYLKGNELKTLP
PGLLTPTPKLEKLSLANNNLTELPAGLLNGLENLD
TLLLQENSLYTIPKGFFGSHLLPFAFLHGNPWLCN
CEILYFRRWLQDNAENVYVWKQGVDVAAMTSNVAS
VQCDNSDKFPVYKYPGKGCPTLGDEGDTDLYDYYP
EEDTEGDKVR QATEYEYLDYDFLPETEPPICEVSKVASHLEVNCD  (SEQ ID NO: 7)
KRNLTALPPDLPKDTTILHLSENLLYTFSLATLMP
YTRLTQLNLDRCELTKLQVDGTLPVLGTLDLSHNQ
LQSLPLLGQTLPALTVLDVSFNRLTSLPLGALRGL
GELQELYLKGNELKTLPPGLLTPTPKLEKLSLANN
NLTELPAGLLNGLENLDTLLLQENSLYTIPKGFFG
SHLLPFAFLHGNPWLCNCEILYFRRWLQDNAENVY
VWKQVVDVKAVTSNVASVQCDNSDKFPVYKYPGKG
CPTLGDEGDTDLYDYYPEEDTEGDKVR
```

A glycoprotein protein variant can be provided as part of a fusion protein. For example, glycoprotein Ibα protein-immunoglobulin fusion proteins are useful for inhibiting adherence of platelets and leukocytes to biological tissues, such as for example the vascular endothelium. The fusion proteins of the invention, or nucleic acids encoding these fusion proteins, can be incorporated into pharmaceutical compositions and administered to a subject to inhibit an interaction between an glycoprotein Ibα ligand (such as von Willebrand Factor, Mac-1, P-selectin or thrombin) and an glycoprotein Ibα protein on the surface of a cell, such as a platelet. Inhibition of binding suppresses glycoprotein Ibα protein-mediated platelet aggregation and associated signal transduction in vivo.

An example of a GPIbα fusion protein is the amino acid sequence with SEQ ID NO:7, above, in which amino acids 1-18 are from a non-GPIbα polypeptide and the remainder of the polypeptide has the amino acids sequence of a GPIbα polypeptide.

The glycoprotein Ibα protein-immunoglobulin fusion proteins can be used to modulate the bioavailability of a glycoprotein Ibα protein cognate ligand. Inhibition of the glycoprotein Ibα protein ligand/glycoprotein Ibα protein interaction are useful therapeutically for, inter alia, the treatment of vascular inflammation and other vascular disorders associated with platelet activation.

Glycoprotein Variant Ibα Fusion Polypeptides

In various aspects the invention provides fusion proteins that include a first polypeptide containing at least a portion of a glycoprotein Ibα polypeptide variant operatively linked to a second polypeptide. As used herein, a glycoprotein Ibα "fusion protein" or "chimeric protein" includes at least a portion of a glycoprotein Ibα polypeptide variant operatively linked to a non-glycoprotein Ibα polypeptide. An "glycoprotein Ibα polypeptide" or "glycoprotein Ibα polypeptide variant" refers to a polypeptide having an amino acid sequence corresponding to at least a portion of a glycoprotein Ibα polypeptide, whereas a "non-glycoprotein Ibα polypeptide" refers to a polypeptide having an amino acid sequence corresponding to a protein that is not substantially homologous to the glycoprotein Ibα protein, e.g., a protein that is different from the glycoprotein Ibα polypeptide or fragment and that is derived from the same or a different organism. Within a glycoprotein Ibα fusion protein the glycoprotein Ibα polypeptide can correspond to all or a portion of an Ibα protein.

In one embodiment, a glycoprotein Ibα fusion protein comprises at least one biologically active portion of a glycoprotein Ibα protein. In another embodiment, a glycoprotein Ibα fusion protein comprises at least two biologically active portions of a glycoprotein Ibα protein. In yet another embodiment, a glycoprotein Ibα fusion protein comprises at least three biologically active portions of a glycoprotein Ibα protein. Within the fusion protein, the term "operatively linked" is intended to indicate that the first and second polypeptides are linked in a manner that allows for at least one function associated with a glycoprotein Ibα polypeptide. When used to refer to nucleic acids encoding a glycoprotein Ibα fusion polypeptide, the term operatively linked means that a nucleic acid encoding the glycoprotein Ibα polypeptide and the non-glycoprotein Ibα polypeptide are fused in-frame to each other. The non-glycoprotein Ibα polypeptide can be fused to the N-terminus or C-terminus of the glycoprotein Ibα polypeptide.

In a further embodiment, the glycoprotein Ibα fusion protein may be linked to one or more additional moieties. For example, the glycoprotein Ibα fusion protein may additionally be linked to a GST fusion protein in which the glycoprotein Ibα fusion protein sequences are fused to the C-terminus of the GST (i.e., glutathione S-transferase) sequences. Such fusion proteins can facilitate the purification of glycoprotein Ibα fusion protein.

In another embodiment, the fusion protein includes a heterologous signal sequence (i.e., a polypeptide sequence that is not present in a polypeptide encoded by a glycoprotein Ibα nucleic acid) at its N-terminus. For example, the native glycoprotein Ibα signal sequence can be removed and replaced with a signal sequence from another protein. In certain host cells (e.g., mammalian host cells), expression and/or secretion of glycoprotein Ibα can be increased through use of a heterologous signal sequence. A representative signal sequence is MPLLLLLLLLPSPLHP (SEQ ID NO:8). Another representative signal sequence is MPLQLLLL-LILLGPGNSLQL WDTWADEAEK ALGPLLARDRR (SEQ ID NO:9). If desired, one or more amino acids can additionally be inserted between the first polypeptide moiety comprising the GP Ibα moiety and the second polypeptide moiety.

An chimeric or fusion protein of the invention can be produced by standard recombinant DNA techniques. Nucleic acid sequences encoding GPIbα polypeptides, as well as the amino acid sequences of these polypeptides, from which variant GPIbα polypeptide variants are constructed are disclosed in WO02/063003, the contents of which are incorporated herein by reference in their entirety.

For example, DNA fragments coding for the polypeptide variant sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A glycoprotein Ibα encoding nucleic acid can be cloned into such an expression vector such that the fusion moiety is linked in-frame to the immunoglobulin protein.

Glycoprotein Ibα fusion polypeptides may exist as oligomers, such as dimers or trimers. In some embodiments, the glycoprotein Ibα fusion polypeptide is a dimer.

In some embodiments, the GP Ib α polypeptide moiety is provided as a variant GP Ib α polypeptide having a mutation in the naturally-occurring GP Ib α sequence (wild type) that results in higher affinity (relative to the non-mutated sequence) binding of the GP Iβα polypeptide to a leukocyte cell surface molecule. For example, the mutant polypeptide may bind with higher affinity to von Willebrand factor (vWF). This increased reactivity, or hyperresponsiveness, can be assessed using low concentrations of ristocetin. Alternately, any other suitable means for determining the reactivity of the polypeptide with vWF can also be utilized to identify polypeptides which are "more" reactive with vWF, i.e. more reactive than naturally-occurring wild-type GP Ibα. Examples of GP Ib α polypeptide variants that bind with higher affinity to vWF include GP Ibα variants that include sequence alterations in the hinge region of a GP Ibα polypeptide. The hinge region is defined as the region including residues 220 to 310 and is reported to be a major binding site for vWF within the GP Ib α polypeptide. Mutations in the hinge region include those at residue 233, which in the wild-type GP Ib α encodes glycine. An example of a suitable substitution of is one in which the glycine at position 233 is replaced with valine (i.e., G233V). A second site for mutation at the hinge region is at residue 239, which in the wild-type GP Ib α encodes methionine. A substitution of valine for methionine 239 is a representative substitution, but other amino acids can also be substituted. In addition, hinge region variants of GP Ib α polypeptides suitable for use in a fusion polypeptide of the invention have mutations at residue both positions 233 and 239. (see e.g., Dong et al., JBC 275:36 27663-27670 (2000)) Thus, the invention includes fusion proteins that have a substitution at position 239, e.g., an M239V substitution of a variant GP Ib α polypeptide. Also within the invention is a fusion protein having a substitution at position 233, e.g., G233V, and a fusion protein that includes a variant GP Ib α polypeptide with positions at both 233 and 239, e.g, a G233V and M239V substitution.

In some embodiments, the first polypeptide includes a full-length GP Ib α polypeptide. Alternatively, the first polypeptide comprise less than fill-length GP Ib α polypeptide. For example the first polypeptide less than 600 amino acids in length, e.g., less than or equal to 500, 250, 150, 100, 50, or 25 amino acids in length.

In some embodiments, the second polypeptide is soluble. In some embodiments, the second polypeptide enhances the half-life, (e.g., the serum half-life) of the linked polypeptide. In some embodiments, the second polypeptide includes a sequence that facilitates association of the fusion polypeptide with a second GP Ib α polypeptide. In some embodiments, the second polypeptide includes at least a region of an immunoglobulin polypeptide. Immunoglobulin fusion polypeptide are known in the art and are described in e.g., U.S. Pat. Nos. 5,516,964; 5,225,538; 5,428,130; 5,514,582; 5,714,147; and 5,455,165.

In some embodiments, the second polypeptide comprises a full-length immunoglobulin polypeptide. Alternatively, the second polypeptide comprise less than full-length immunoglobulin polypeptide, e.g., a heavy chain, light-chain, Fab, $Fab_2$, Fv, or Fc. For example, in some embodiments the second polypeptide includes the heavy chain of an immunoglobulin polypeptide. In further embodiments, the second polypeptide includes the Fc region of an immunoglobulin polypeptide.

In another aspect of the invention, the second polypeptide has less effector function that the effector function of a Fc region of a wild-type immunoglobulin heavy chain. Fc effector function includes for example, Fc receptor binding, complement fixation and T cell depleting activity (see, for example, U.S. Pat. No. 6,136,310). Methods of assaying T cell depleting activity, Fc effector function, and antibody stability are known in the art. In one embodiment the second polypeptide has low or no affinity for the Fc receptor. In an alternative embodiment, the second polypeptide has low or no affinity for complement protein C1q.

A representative second polypeptide sequence includes the amino acid sequence of SEQ ID NO:10. This sequence includes a Fc region. Underlined amino acids are those that differ from the amino acid found in the corresponding position of the wild-type immunoglobulin sequence:

HTCPPCPAPEALGAPSVFLFPPKPKDTLMISRTP (SEQ ID NO: 10)

EVTCVVVDVSHEDPEVKFNWYVDGVEVHNAKTKP

REEQYNSTYRVVSVLTVLHQDWLNGKEYKCKVSN

KALPVPIEKTISKAKGQPREPQVYTLPPSREEMT

KNQVSLTCLVKGFYPSDIAVEWESNGQPENNYKT

TPPVLDSDGSFFLYSKLTVDKSRWQQGNVFSCSV

MHEALHNHYTQKSLSLSPGK

The GPIbα polypeptide variants can include, in addition to the designated substituted amino acid substitution, an alternative amino acid that fulfills the same function as the designated acid. In some embodiments, the alternative amino acid is related to the designated amino acid as a conservative amino acid substitution of the indicated amino acid. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Thus, in some embodiments, rather than replacing a tyrosine with a phenylalanine at position 276, 278, or 279 (Y276F, Y278F, or Y279F), the tyrosine residue can be replaced with tryptophan or histidine. Similarly, for the C65S variant, the cysteine may alternatively be replaced with glycine, asparagine, glutamine, threonine, or tyrosine. For the L237V substitution, the leucine may alternatively be replaced with alanine, isoleucine, proline, phenylalanine, methionine, or tryptophan.

The invention also includes a polypeptide whose sequence that are 80%, 85%, 90%, 95%, 98%, or 99% homologous to the sequence disclosed in SEQ ID NO:1 or SEQ ID NO:2, provided that it includes one or more of the amino acid substations C65S, K237V, Y276F Y278F, Y279F, K237V. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (e.g., an identity of 80-99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman.

Another aspect of the invention pertains to vectors (including expression vectors) containing a nucleic acid encoding glycoprotein Ibα fusion polypeptides, or derivatives, fragments, analogs or homologs thereof. Recombinant expression vectors of the invention can be designed for expression of glycoprotein Ibα fusion polypeptides in prokaryotic or eukaryotic cells.

In another embodiment, the glycoprotein Ibα fusion polypeptide expression vector is a yeast expression vector. Examples of vectors for expression in yeast *Saccharomyces cerevisiae* are known in the art.

Alternatively, glycoprotein Ibα fusion polypeptide can be expressed in insect cells using methods known in the art, e.g., with baculovirus expression vectors.

In yet another embodiment, a nucleic acid of the invention is expressed in mammalian cells using a mammalian expression vector.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art.

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to a glycoprotein Ibα fusion polypeptide mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

A host cell can be any prokaryotic or eukaryotic cell. For example, glycoprotein Ibα fusion polypeptides can be expressed in bacterial cells such as E. coli, insect cells, yeast or mammalian cells (such as human, Chinese hamster ovary cells (CHO) or COS cells). Other suitable host cells are known to those skilled in the art.

Vector DNA can be introduced into prokaryotic or eukaryotic cells via conventional transformation or transfection techniques.

Mammalian host cell, such as a Chinese hamster ovary cells (CHO) or COS cells can be transfected with expression vectors to enable, via posttranslational modification, the generation of the sialyl Lewis$^x$ epitope on the N-linked and O-linked glycans of glycoprotein Ibα fusion polypeptides. In the case of CHO cells this requires the co-expression of an α-1,3/1,4 fucosyltranseferase (Kukowska-Latallo et al., Genes Dev. 4:1288-303, 1990) and Core2 beta-1,6-N-acetyl-glucosaminyltransferase enzymes. (Kumar et al., Blood 88:3872-79, 1996). The presence of the sialyl Lewis$^x$ epitopes on the N-linked and O-linked glycans of glycoprotein Ibα fusion polypeptides will enhance the binding to selectins.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding glycoprotein Ibα fusion polypeptides or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) glycoprotein Ibα fusion polypeptides. Accordingly, the invention further provides methods for producing glycoprotein Ibα fusion polypeptides using the host cells of the invention. In one embodiment, the method comprises culturing the host cell of invention (into which a recombinant expression vector encoding glycoprotein Ibα fusion polypeptides has been introduced) in a suitable medium such that glycoprotein Ibα fusion polypeptides is produced. In another embodiment, the method further comprises isolating glycoprotein Ibα fusion polypeptide from the medium or the host cell.

The fusion polypeptides may be isolated and purified in accordance with conventional conditions, such as extraction, precipitation, chromatography, affinity chromatography, electrophoresis or the like.

Chemical synthesis of polypeptides facilitates the incorporation of modified or unnatural amino acids, including D-amino acids and other small organic molecules. Replacement of one or more L-amino acids in a peptide with the corresponding D-amino acid isoforms can be used to increase the resistance of peptides to enzymatic hydrolysis, and to enhance one or more properties of biologically active peptides, i.e., receptor binding, functional potency or duration of action.

Introduction of covalent cross-links into a peptide sequence can conformationally and topographically constrain the polypeptide backbone. This strategy can be used to develop peptide analogs of the fusion polypeptides with increased potency, selectivity and stability. Because the conformational entropy of a cyclic peptide is lower than its linear counterpart, adoption of a specific conformation may occur with a smaller decrease in entropy for a cyclic analog than for an acyclic analog, thereby making the free energy for binding more favorable. Macrocyclization is often accomplished by forming an amide bond between the peptide N- and C-termini, between a side chain and the N- or C-terminus [e.g., with $K_3Fe(CN)_6$ at pH 8.5], or between two amino acid side chains. Disulfide bridges are also introduced into linear sequences to reduce their flexibility. Furthermore, the replacement of cysteine residues with penicillamine (Pen, 3-mercapto-(D) valine) has been used to increase the selectivity of some opioid-receptor interactions.

Pharmaceutical Compositions Including Glycoprotein Ibα Fusion Polypeptides or Nucleic Acids Encoding Same The glycoprotein Ibα fusion proteins, or nucleic acid molecules encoding these fusion proteins, (also referred to herein as "Therapeutics" or "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The active agents disclosed herein can also be formulated as liposomes. Liposomes are prepared by methods known in the art. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents can be included in the composition, for example, sugars, polyalcohols such as manitol and sorbitol; and sodium chloride. Prolonged absorption of the injectable compositions can be brought about by including in the composition an agent which delays absorption, for example, aluminum monostearate and gelatin.

Sterile injectable solutions can be prepared by incorporating the active compound (e.g., a glycoprotein Ibα fusion protein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

In some embodiments, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration or by stereotactic injection. The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Sustained-release preparations can be prepared, if desired. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Methods of Inhibiting Adherence of in a Biological System

Included in the invention is a method of inhibiting adherence of a blood cell to a biological tissue in a biological system. The method includes adding to a biological system a fusion polypeptide of the invention in an amount sufficient to inhibit adherence of a blood cell to the biological tissue.

The blood cell can be for example, a leukocyte, platelet or red blood cell. The leukocyte can be any leukocyte that is capable of adhering to a biological tissue. In various aspects the leukocyte is a granulocyte, (i.e., neutrophil, basophil or eosinohil), monocyte (i.e., macrophage) or lymphocyte (e.g., T-lymphocyte, B-lymphocyte, tumor infiltrating lymphocytes or natural killer cell). In some embodiments, the leukocytes express a β2 intergin, e.g. Mac-1. Alternately, the leuckocyte expresses a selectin ligand.

Also included in the inventions are methods of inhibiting adherence of a protein to a biological tissue in a biological system. The method includes adding to a biological system a fusion polypeptide of the invention in an amount sufficient to inhibit adherence of the protein to the biological tissue.

The protein can be membrane associated (e.g., covalently, non-covalently, or ionic). Alternatively, the protein can be in a soluble form (i.e., in solution). The protein is von Willebrand Factor, thrombin, P-selectin of glycoprotein Ibα.

As used herein a biological system is meant to include any system that comprises biological components, e.g., cells, proteins, carbohydrates, lipids or nucleic acids. The biological system can be an in vivo, ex vivo or in vitro system.

"Adherence" is meant to include any biological interaction of a leukocyte, e.g., rolling, firm attachments or specific interaction.

Inhibition of adherence of a blood cell or protein to a biological tissue can be measured using methods known in the art. For example, assays for detecting binding of glycoprotein Ibα to a biological tissue are described in Simon et al., J. Exp. Med. 192:193-204, 2000, and references cited therein. In various embodiments, binding of a GP Ib α fusion protein inhibits binding of a blood cell or protein to a biological tissue by at least 30%, 50%, 75%, 90%, 95%, 99% or 99.9%.

Adherence can also be assessed in condition of greater or less than physiological flow conditions, including static conditions and serial application of static and shear conditions. Adherence can be determined for example colormetrically, fluorometrically, by flow cytometry or using a parallel plate flow chamber assay.

Also included in the invention are methods of treating platelet activation associated disorders in a subject by administering to a subject a biologically-active therapeutic compound (hereinafter "Therapeutic"). Alternatively, the subject is also administered one or more of the following: a statin; acetylsalicylic acid (aspirin); heparin (including unfractionated or low-molecular weight heparins); glycoprotein IIb/IIIa antagonists; clopidogrel; P-selectin antagonists; thrombin inhibitors; and thrombolytic enzymes.

The subject can be e.g., any mammal, e.g., a human, a primate, mouse, rat, dog, cat, cow, horse, pig.

The therapeutics include, e.g.: (i) any one or more of the glycoprotein Ibα polypeptide and derivative, fragments, analogs and homologs thereof; (ii) antibodies directed against the glycoprotein Ibα polypeptides described in (i) and (iii) nucleic acids encoding a glycoprotein Ibα polypeptide, and derivatives, fragments, analogs and homologs thereof as described in (i) above.

Essentially any disorder that is etiologically linked to platelet activation is considered amenable to prevention or to treatment. The disorder can be, e.g., vascular inflammation; atherosclerosis; restenosis (e.g., angioplasty-related restenosis); and/or a condition associated with thrombotic disease, e.g., angina, (including stable angina and unstable angina) acute myocardial infarction, stroke, venous thrombosis or arterial thrombosis.

The invention will be further illustrated in the following non-limiting examples.

EXAMPLE 1

GPIb-Ig Tyrosine Sulfation Plays an Important Role in Thrombin Binding but is Less Important for vWF Binding The role of the acidic carboxyl terminal region of GPIbα in binding to vWF and thrombin was examined by tyrosine residues at positions 276, 278, and/or 279 of three types of GPIbα-IgG$_1$Fc fusion proteins: those with a wild-type human GPIbα sequence; a fusion protein with the M239V (1V) substitution, and a fusion protein with a double G233V M239V (2V) substitution. The proteins were produced in Chinese Hamster Ovary (CHO) cells, then isolated by Protein A affinity chromatography and anion exchange chromatography. Dimerized forms of the fusion proteins in which the sulfation state varied from 0 to 6 were isolated.

Binding of the isoforms to the vWF A1 domain (A1), to intact vWF, and to α-thrombin was examined using surface plasmon resonance (BiaCore).

The 1V and 2V polypeptides bound with significantly higher affinity to the A1 domain as compared to the WT polypeptides. The 1V and 2V polypeptides also showed significantly enhanced affinity for intact vWF relative to the affinity of the fusion protein with the wild-type GPIbα sequence for vWF The $K_d$ for the 2V variant ranged from 4 nm to 12 nm, and the $K_d$ for the 1V variant ranged from 119 nm to 284 nM for fully sulfated to non-sulfated isoforms. Binding of wild-type GPIbα to vWF was not detected under the same conditions, which indicates a Kd>1 mM. Varying the sulfation state in WT, 1V, and 2V did not correlate with a significant change in binding to A1 domain or intact vWF. Finally, the GPIbα-Ig-vWF interaction exhibited slow-on/slow-off kinetics typical of a hydrophobic interaction ($K_a$ and $K_d \sim 10^5 M^{-1} s^{-1}$ and $\sim 10^{-3} s^{-1}$, respectively).

For GP Ibα-Ig239V and GP Ib-Ig2V molecules, the binding affinity of the fully sulfated isoform to thrombin was ~80-fold higher than that of the unsulfated isoform ($K_D$ of 0.5 µM and 40 µM, respectively). For vWF binding, the fully sulfated molecules were only 3-4 fold more active than the unsulfated forms of both mutants ($K_D$=3.4-15 nM for 2V 6-0 sulfated, 113-521 nM for 1V 6-0 sulfated). The relationship between sulfation state and binding to von Willebrand Factor and binding to thrombin was also examined.

Rat tail bleeding method: Adult male Sprague Dawley rats (Taconic), weighing 250-300 gm, were used. The animals were equipped with a jugular vein catheter by the vendor before arriving. The animals were housed in individual cages at room temperature under a light period of 12 hr (6:am-6:pm) at our institutional animal facility and were provided standard laboratory rodent chow and water ad libitum. The animals were acclimated to their new environment at least three days before the use.

GPIb-Ig sample administration and rat Tail vein bleeding procedures: On the day of the experiment, an extension tubing (20 cm of PE 50 tubing) with a 3-way stopcock and a 1-cc syringe filled with sterile isotonic 0.9% saline was attached to the indwelling jugular vein catheter. Stock GPIb-Ig test sample was diluted with isotonic 0.9% saline and was administered at indicated doses in a volume of 0.1 ml per 100 gm body weight via another arm of the 3-way stopcock. The catheter was flushed with 0.2 ml of saline. Ten minutes after the injection, the rats were removed from their home cage and were gently put into a restrainer. The distal 1-2 mm segment of the tail was transected using a razor blade and the tail was quickly immersed into a 300 ml-beaker pre-filled with 0.9% isotonic saline (temperature 37° C.). Bleeding time was defined as the period of time from the start of the tail bleeding to completely cease of bleeding (no re-bleeding within 30 second once the bleeding has stopped). At the end of the experiment, the rats were euthanized by inhalation of $CO_2$.

In the rat tail bleeding assay, 10 minutes following an i.v. dose of 200 ug/kg, bleeding time of four minutes was detected in GPIbα variants with a sulfation state 0, 1, or 2. Bleeding time increased as the sulfation state increased to 6, where bleeding time was 10 minutes.

These data demonstrate that sulfation plays a role in thrombin binding, but a much lesser role in vWF binding. However, the sulfation state significantly affects binding to α-thrombin. The stoichiometry of GPIbα-Ig binding with thrombin was greater than 2 α-thrombin per GPIbα-Ig. The α-thrombin-GPIbα interaction is much more sensitive to the GPIbα-Ig sulfation state compared with the hyrdophobicity of the Cys208-Cys249 loop of GPIbα, which binds vWF. These results indicate that the GPIbα contains two functionally distinguishable subdomains: one for vWF binding and one for thrombin binding.

EXAMPLE 2

Cys 65 in GPIba is Involved in Aggregation

The crystal structure reveals that Cys65 of GPIbα is buried in the LRR region. The very low labeling ratio (about 5%) with thiol-reactive probes under native conditions demonstrated the inaccessibility of this Cys residue. Ellman's assay and preliminary native peptide mapping showed that there was no modification on Cys65. However, even a very small amount of exposed thiol could form intermolecular disulfide bonds and caused aggregation. The role of this residue in aggregation was examined.

When GP Ibα sample was stressed at 40° C. for 80 hrs, about 25% of total protein formed aggregates. The aggregates were reducible but mostly SDS stable. Analytical ultracentrifugation indicated that the aggregates ranged from dimer to octamer. Non-reduced, alkylated Achro-K peptide map of the aggregates showed that the free Cys-containing peptide (K4 peptide) disappeared in the map, which might form a large peptide with another K4 and other Cys containing peptides. To confirm the role of the free Cys in aggregation, the GPIbα sample was heat-stressed in 1 M GnHCl which resulted in total covalent aggregation. In the presence of 1M GnHCl, the protein structure is likely to be loosened, thereby exposing the buried Cys65, and accelerating the aggregation. These data suggest that under these conditions the free Cys residue can be involved in aggregation.

EXAMPLE 3

GPIbα Fusion Proteins Interact with vWF Polypeptide

Evidence for a direct interaction between a GPIbα fusion protein variants and vWF polypeptide was examined.

The GPIbα fusion protein variants tested included 1V, 2V, 3V, 3V/C65S, 2V/FFF, and a variant named "clipped 2V". Control reactions included a 290 amino acid GPIbα protein, a vWF polypeptide alone or an irrelevant control polypeptide (47.mFc, a PSGL-1 fusion protein).

A fusion polypeptide or control polypeptide was mixed with Protein A Sepharose beads, which bound to the immunoglobulin moieties of the fusion protein. Protein bound to the Protein A Sepharose beads were eluted and electrophoresed through a 3-8% Tris-Acetate gel. The gel was then immunoblotted with a polyclonal antibody to vWF, and the antibody detected. Gels were run under both reducing and non-reducing conditions. The procedure was performed twice.

The results of binding to the vWF A1 fragment or to intact vWF fragment are shown below. vWF showed the strongest binding to the GPIBα variants 3V and 3V/C65S when assayed under both reducing and non-reducing conditions. Strong binding was also observed with the 2V variant, while comparatively less binding was detected with the 1V variant and the 2V/FFF variant. The GPIbα wild-type polypeptide showed weak binding to vWF in these experiments.

| | 1V | 2V | 3V | 2V/FFF | 3V/C-S |
|---|---|---|---|---|---|
| vWF A1 Binding Constant ($K_A$, $M^{-1}$) | 3.6E+07 | 1.9E+08 | 1.5E+09 | 9.1E+07 | 1.5E+09 |

-continued

|  | 1V | 2V | 3V | 2V/FFF | 3V/C-S |
|---|---|---|---|---|---|
| vWF Binding Constant ($K_A$, $M^{-1}$) | 7.7E+07 | 5.6E+08 | 1.7E+09 | 2.4E+08 | 1.7E+09 |

EXAMPLE 5

In vivo Inhibition of Repetitive Coronary Artery Thrombosis

The ability of a fusion Ibα protein-immunoglobulin protein to inhibit coronary artery thrombosis in vivo is determined using the procedure described by Folts at al., Circulation 54:365-70, 1976 is examined. The fusion protein includes a GPIbα sequence with the substitutions G233V K237V and M239V relative to the amino acid sequence of SEQ ID NO:1.

Mongrel dogs, weighing 20-25 kg, are anesthetized with sodium pentobarbital (30 mg/kg i.v.), then intubated and ventilated with room air using a respirator. Venous and arterial catheters are placed. The heart is approached by left thoracotomy through the fifth intercostal space. The pericardium is opened and sutured to the wound edges to provide a cradle without displacing the heart. About 2 cm of the left circumflex coronary artery (LCX) is isolated. Mean and dynamic LCX flow are continuously monitored using a perivascular ultrasonic flow probe placed proximally on the artery. After a stabilization period, the endothelium of the LCX is injured by squeezing with a hemostat. A plastic constrictor is placed distal and overlying the area of injured endothelium to provide approximately 70-80% vessel stenosis. When blood flow decreases to zero, the blood flow is restored by shaking the constrictor to dislodge aggregated platelets. This decrease and restoration of blood flow are termed CFRs. At least five consecutive CFRs are recorded prior to administering the test drug.

Increasing amounts of 3V results in higher blood flow. These results demonstrate that the fusion glycoproteins inhibit thrombosis in the animal model.

EXAMPLE 6

In Vivo Treatment of a Subject with of Unstable Angina (UA) or Non-ST-Elevated Myocardial Infarction (NSTEMI)

A GPIBα-Ig variant according to the invention is administered as a fusion protein by a single intravenous bolus injection (10 mg) to a patient with unstable angina or non-ST-elevated myocardial infarction (NSTEMI). Treatment with the variant ameliorates the UA or NSTEMI. The ristocetin induced platelet aggregation assay (RIPA) is used to monitor GPIb-Ig activity.

EXAMPLE 7

Comparison of Bleeding Times Using Clopidogrel and GPIbα 2V or GPIbα 2V/FFF Variants The effect on bleeding time was examined by comparing bleeding times in rats treated with clopidogrel and GPIbα 2V or two different doses of GPIba 2V/FFF, which lack thrombin binding sites.

The GPIbα variant was administered intravenously two hours after administration of clopidogrel (4.3 mg/kg, po). GPIbα variants tested included GPIbα 2V/290/FFF GPIba 2V/290 GPIba 2V/290 GPIba 2V/290, GPIba 2V/290/FFF (100 mcg/kg), and GPIba 2V/290 (50 mcg/kg). RBT was measured 15 minutes after administration of the GPIα variant. Six or seven animals were tested for each treatment.

Bleeding time increased from 8.2 minutes (N=7) in rats treated with clopidogrel alone to 24 minutes in rats treated with clopidogrel and 50 mcg/kg of GPIbα 2V/290 (N=6). Bleeding time increased to 13.9 minutes in rats treated with 50 mcg/kg of GPIba 2V/290/FFF (N=6), and to 19 minutes in rats treated with 100 mcg/kg of GPIbα 2V/290/FFF (N=7). Thus, a shorter bleeding time was observed in animals given twice the dose of the GPIbα 2V/290/FFF as compared to animals given the GPIba 2V/290 variant.

EXAMPLE 8

Comparison of Antithrombotic Efficacy of Sulfated and Non-Sulfated Forms of Recombinant Soluble GPIba Chimeras in a Canine Model of Coronary Artery Thrombosis The ligand binding capacity and anti-thrombotic efficacy of a non-sulfated recombinant human GPIbα chimera (GPIb-290/2V/FFF-Ig) was compared to that of a sulfated recombinant human GPIbα chimera (GPIb-290/2V-Ig).

Soluble recombinant GPIbα Chimeras used included GPIb-290/2V-Ig, which consists of the N-terminal 290 amino acids of GPIba with gain-of-function valine substitutions at positions 233 and 239, fused to a human IgG1 Fc domain. GPIbα-290/2V/FFF-Ig was generated by further substituting three tyrosine residues (Tyr-276, 278, 279) with phenylalanines to eliminate sulfation.

Cyclic flow reductions (CFRs) were induced by crush injury of the left circumflex coronary artery in anesthetized male mongrel dogs. Coronary blood flow was continuously monitored using a perivascular ultrasonic flow probe. The template bleeding time was measured at the surface of the inner upper lip using an automated cutting device. The bleeding time prolongation caused by sulfated and non-sulfated GPIba chimeras was assessed by using rat tail bleeding model. Platelet function in whole blood before and at various time points after treatment in Folts' model was measured with a Platelet Function Analyzer-100 (PFA-100).

The binding abilities of GPIbα-290/2V-Ig and GPIbα-290-2V/FFF-Ig to vWF and a-thrombin were evaluated in vitro using a Biacore assay. The results are presented below:

| Mutant | vWFA1 Binding | Thrombin Binding |
|---|---|---|
| GPIb wild type | 266 nM | 0.76 uM |
| GPIb-290/2V-Ig | 5 nM | 0.63 uM |
| GPIb-290/2V/FFF-Ig | 15.4 nm | 35.8 uM |

The effect of wild-type, or GPIb chimeras on ristocetin-induced human platelet aggregation is shown in FIG. 1. Shown are wild-type GPIba ("Normal"), GPIb-Ig WT, GPIba-290/2V-Ig, and GPIba-290/2V/FFF-Ig.

The dose response of GPIb-290/2V-Ig ("2V") and GPIb-290/FFF-Ig ("FFF") in a canine Folts' model of coronary thrombosis is shown below. A score of 4 was given if CFRs were completely eliminated, and a score of 3 was given if the CFRs were not completely abolished, but the coronary was able to spontaneously open.

| 2V (ug/kg, iv) | Response Score | BT (min) | FFF (ug/kg, iv) | Response Score | BT (min) |
|---|---|---|---|---|---|
| 50 | 4 (6/6) | 2.0 | 50 | 3 (3/3) | 2.4 |
| 100 | 4 (6/6) | 3.7 | 100 | 4 (3/3) | 2.3 |
| — | — | — | 200 | 4 (3/3) | 3.1 |
| 500 | 4 (2/2) | 10.25 | 500 | 4 (3/3) | 5.4 |

Rat tail bleeding time prolongation caused by GPIb-290/2V-Ig and GPIb-290/2V/FFF-Ig was also examined:

| 2V (ug/kg, iv) | BT Mean (±SE) | N | FFF (ug/kg, iv) | BT Mean (±SE) | N |
|---|---|---|---|---|---|
| 50 | 3.1 ± 0.6 | 8 | 100 | 3.3 ± 0.4 | 6 |
| 100 | 4.6 ± 0.8 | 8 | 200 | 4.9 ± 0.2 | 7 |
| 200 | 8.9 ± 1.1 | 7 | 500 | 8.7 ± 0.7 | 7 |

Figure 2:
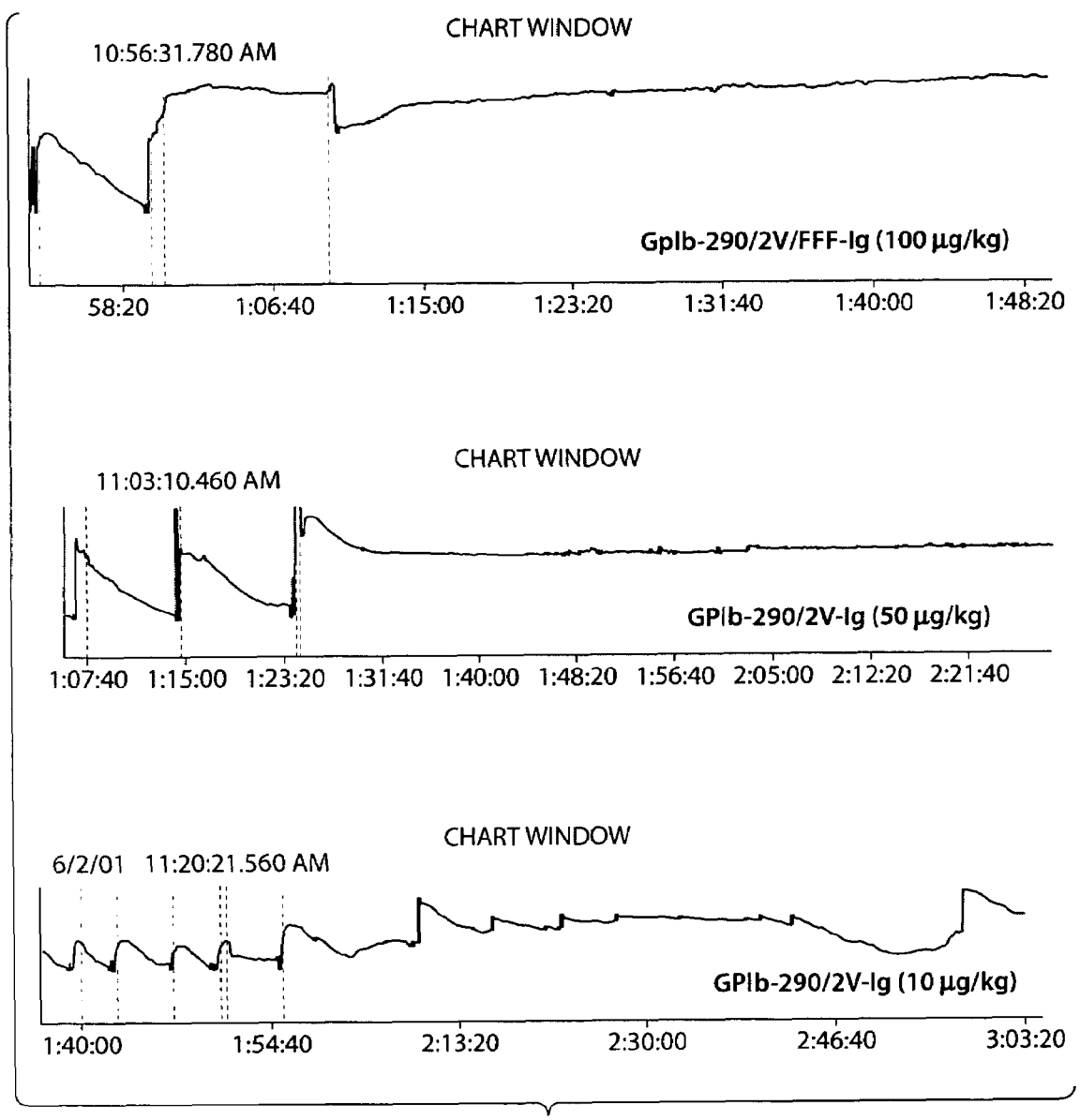
FIG. 2 is a graph showing the antithrombotic efficacy of GPIbα chimeras in a canine Folts' model of coronary thrombosis (y-axis: LCX blood).

FIG. 2 is a graph showing the antithrombotic efficacy of GPIbα chimeras in a canine Folts' model of coronary thrombosis (y-axis: LCX blood).

Figure 3:
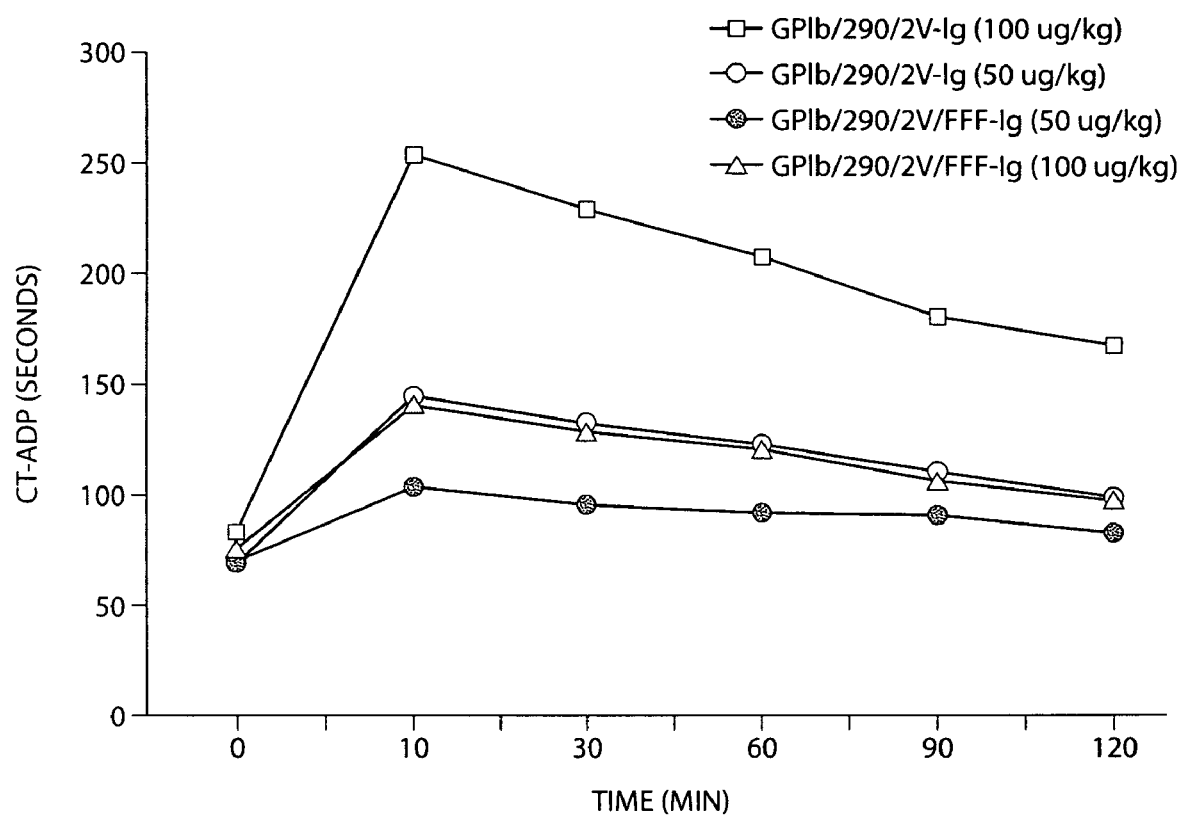
FIG. 3 is a graph showing inhibition of platelet function by GPIb/290/2V-Ig and GPIb/290/2V/FFF-Ig in a canine model of coronary thrombosis assessed by PFA-100.

FIG. 3 is a graph showing inhibition of platelet function by GPIb/290/2V-Ig and GPIb/290/2V/FFF-Ig in a canine model of coronary thrombosis assessed by PFA-100.

These results demonstrate that conversion of the six sulfated tyrosines to phenylalanines decreases vWF A1 domain binding by ~3-fold in these studies and almost completely abrogated thrombin binding. GPIb/290/2V/FFF-Ig demonstrated a 50% decrease in potency as compared with GPIb-290/2V-Ig in cyclic flow reduction, bleeding time prolongation and ADP closure times assessed using a PFA-100. The prevention of arterial thrombus formation by GPIba chimeras at these doses occurs via inhibition of the vWF A1 domain, and this activity is independent of a thrombin binding.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polypeptide comprising SEQ ID NO: 2, provided said polypeptide comprises substitutions K237V and C65S;
    wherein said polypeptide binds to von Willebrand factor with an affinity that is at least 10-fold higher than a GP1bα polypeptide comprising SEQ ID NO: 1; and
    wherein said polypeptide has at least one activity selected from the group consisting of:
    1) lower affinity binding to alpha thrombin relative to binding to alpha thrombin of a protein sequence with the amino acid sequence of SEQ ID NO: 2;
    2) lower aggregation relative to aggregation of a protein sequence with the amino acid sequence of SEQ ID NO: 2; and
    3) increased resistance to proteolysis relative to a protein sequence with the amino acid sequence of SEQ ID NO: 2.

2. The polypeptide of claim 1, wherein said polypeptide is provided as a fusion protein.

3. The fusion protein of claim 2 comprising a region of an immunoglobulin.

* * * * *